United States Patent
Tang et al.

(10) Patent No.: US 9,662,084 B2
(45) Date of Patent: May 30, 2017

(54) METHOD AND APPARATUS FOR ITERATIVELY RECONSTRUCTING TOMOGRAPHIC IMAGES FROM ELECTROCARDIOGRAPHIC-GATED PROJECTION DATA

(71) Applicant: TOSHIBA MEDICAL SYSTEMS CORPORATION, Otawara-shi (JP)

(72) Inventors: Qiulin Tang, Buffalo Grove, IL (US); Satoru Nakanishi, Arlington Heights, IL (US)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/743,731

(22) Filed: Jun. 18, 2015

(65) Prior Publication Data

US 2016/0367212 A1   Dec. 22, 2016

(51) Int. Cl.
| | |
|---|---|
| G06K 9/00 | (2006.01) |
| A61B 6/00 | (2006.01) |
| A61B 6/03 | (2006.01) |
| G06T 11/00 | (2006.01) |
| G06T 7/00 | (2017.01) |

(52) U.S. Cl.
CPC ............ *A61B 6/5288* (2013.01); *A61B 6/032* (2013.01); *G06T 7/0012* (2013.01); *G06T 11/006* (2013.01); *G06T 2207/10081* (2013.01); *G06T 2207/30048* (2013.01); *G06T 2211/421* (2013.01); *G06T 2211/424* (2013.01)

(58) Field of Classification Search
USPC ............................................. 382/128–134
See application file for complete search history.

(56) References Cited

U.S. PATENT DOCUMENTS

| | | | |
|---|---|---|---|
| 7,058,440 B2 | 6/2006 | Heuscher et al. | |
| 7,532,702 B2 | 5/2009 | Hsieh et al. | |
| 8,731,266 B2 | 5/2014 | Zeng et al. | |
| 2006/0198491 A1 | 9/2006 | Taguchi | |
| 2010/0121183 A1* | 5/2010 | Taguchi | A61B 6/5264 600/427 |
| 2013/0279783 A1* | 10/2013 | Schmitt | A61B 6/032 382/131 |

FOREIGN PATENT DOCUMENTS

WO   WO2013002805 A1 *   1/2013   ........... G06T 11/005

OTHER PUBLICATIONS

Qiulin Tang, et al., "A Fully Four-Dimensional, Iterative Motion Estimation and Compensation Method for Cardiac CT," Medical Physics, vol. 39, Issue 7, Jun. 25, 2012.
Daniel Hernandez, et al., "Iterative Image Reconstruction in Spectral-CT," Proceedings of SPIE, vol. 8313, 831330, 2012.

* cited by examiner

*Primary Examiner* — Alex Liew
(74) *Attorney, Agent, or Firm* — Oblon, McClelland, Maier & Neustadt, L.L.P.

(57) ABSTRACT

An apparatus and method for computed tomography (CT) imaging to obtain an image from gated projection data, such as electrocardiographic gated projection data used in cardiac CT. The image reconstruction is performed using an iterative reconstruction method to minimize a cost function including a data-fidelity term (e.g., a system-matrix term) and a regularization term. The system-matrix term includes a weighted inner-product of the system-matrix equation, wherein the weighting matrix includes weighting values to correct the unequal data redundancy of the gated projection data.

20 Claims, 11 Drawing Sheets

METHOD AND APPARATUS FOR ITERATIVELY RECONSTRUCTING TOMOGRAPHIC IMAGES FROM ELECTROCARDIOGRAPHIC-GATED PROJECTION DATA

BACKGROUND

Field

Embodiments disclosed herein relate generally to gated computed tomography (CT) imaging systems and, more particularly, to cardiac-gated CT imaging systems.

Description of the Related Art

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector (and generally many more than one detector) on the opposite side of the body receives radiation transmitted through the body substantially in the projection volume. The attenuation of the radiation that has passed through the body is measured by processing electrical signals received from the detector.

Making projective measurements at a series of different projection angles through the body, a sinogram can be constructed from the projection data, with the spatial dimension of the detector array along one axis and the time/angle dimension along the other axis. In parallel beam CT, the attenuation resulting from a particular volume within the body will trace out a sine wave oscillating along the spatial dimension of the sinogram, with the sine wave being centered on the axis of rotation for the CT system.

The process of X-ray projection measurements of the three-dimensional object onto a two-dimensional measurement plane (or a two-dimensional object onto a one-dimensional measurement plane) can be represented mathematically as a Radon transformation $$g(X,Y)=R[f(x,y,z)],$$

where $g(X,Y)$ is the projection data as a function of position along a detector array, $f(x,y,z)$ is the attenuation of the object as a function of position, and $R[\bullet]$ is the Radon transform. Having measured projection data at multiple angles, the image reconstruction problem can be expressed by calculating the inverse Radon transformation of the projection data $$f(x,y,z)=R^{-1}[g(X,Y,\theta)],$$

where $R^{-1}[\bullet]$ is the inverse Radon transform and $\theta$ is the projection angle at which the projection data was acquired. In practice, there are many methods for reconstructing an image $f(x,y,z)$ from the projection data $g(X,Y,\theta)$.

Often the image reconstruction problem will be formulated as a matrix equation $$Af=g,$$

where g represents the projection measurements of the X-rays transmitted through an object space including the object OBJ, A is the system matrix describing the discretized line integrals (i.e., the Radon transforms) of the X-rays through the object space, and f is the image of object OBJ (i.e., the quantity to be solved for by solving the system matrix equation). The image f is a map of the attenuation as a function of position. Image reconstruction can be performed by taking the matrix inverse or pseudo-inverse of the matrix A. However, this rarely is the most efficient method for reconstructing an image. The more conventional approach is called filtered back-projection (FBP), which, consistent with the name, entails filtering the projection data and then back-projecting the filtered projection data onto the image space, as expressed by $$f(x,y,z)=BP[g(X,Y,\theta)*F_{Ramp}(X,Y)].$$

where $F_{Ramp}(X,Y)$ is a ramp filter (the name "ramp filter" arises from its shape in the spatial-frequency domain), the symbol * denotes convolution, and $BP[\bullet]$ is the back projection function.

Cardiac CT presents particular challenges because, unlike other organs, the heart is constantly pumping to keep blood circulating. Therefore, special methods have developed to perform CT with short time resolution to capture an approximately stationary image of the heart. For example, the advent of subsecond rotation speeds combined with multi-slice CT (up to 320-slices) has enabled high resolution and high-speed CT imaging to be achieve simultaneously, allowing excellent imaging of the coronary arteries (cardiac CT angiography).

As a second example, images with an even higher temporal resolution can be formed using retrospective ECG gating. In this technique, each portion of the heart is imaged more than once while an ECG trace is recorded. The ECG is then used to correlate the CT data with their corresponding phases of cardiac contraction. Once this correlation is complete, all data that were recorded while the heart was in motion (systole) can be ignored and images can be made from the remaining data that happened to be acquired while the heart was at rest (diastole). In this way, individual frames in a cardiac CT investigation have a better temporal resolution than the shortest rotation time, and can even be shorter than the half-scan rotation time.

Even without ECG gating, the temporal resolution of cardiac CT has been aided by the development of short-scan reconstruction methods that do not require projection data corresponding to a complete revolution in order to reconstruct a tomographic image. For example, better time resolution time can be achieved using a half-scan reconstruction, which uses a scan of projection angles spanning $180°+2\gamma$, where $\gamma$ is the half fan angle of the cone-beam/fan-beam. The image reconstruction methods for half-scan CT reconstruction generally differ from full-scan CT reconstruction due to unequal data redundancy for projection rays through the imaged object. Whereas full-scan CT image reconstruction uses conventional FBP, wherein all projection angles are given equal weight, short-scan CT image reconstruction weights each projection angle uniquely, to compensate for unequal sampling of the image object by the measured rays—i.e., unequal data redundancy. This weighting of the projection data in the reconstruction process can be expressed as $$f(x,y,z)=BP[w(X,Y,\theta)g(X,Y,\theta)*F_{Ramp}(X,Y)],$$

wherein $w(X,Y,\theta)$ is the weighting function. There are various approaches to account for variations in the data redundancy, including: the Dreike-Boyd parallel rebinning algorithms, complementary rebinning algorithms, applying suitable weighting function such as the Parker weights to the sinogram, and hybrid techniques.

Similar to the short-scan reconstruction, reconstructing a tomographic image using ECG gating can also involve weighting the projection data to compensate for unequal redundancy in the data.

Even though short-scan and ECG-gated reconstruction have advantages in better temporal resolution, conventional methods of short-scan and ECG-gated reconstruction can also suffer from certain artifacts, such as the banding artifact and low-frequency shading artifacts commonly found in cone-beam reconstruction, as well as poor signal-to-noise ratios (SNR).

BRIEF DESCRIPTION OF THE DRAWINGS

A more complete understanding of this disclosure is provided by reference to the following detailed description when considered in connection with the accompanying drawings, wherein.

DETAILED DESCRIPTION

In one embodiment, there is provided an image-processing apparatus, comprising: processing circuitry configured to (1) obtain projection data representing an irradiance of radiation detected at a plurality of detectors and corresponding to a plurality of projection angles of a radiation source; (2) obtain a gate signal; (3) select a subset of the projection data to be gated projection data corresponding to gated projection angles indicated by the gate signal; determine weighting-and-feathering coefficients according to the gated projections angles; and (4) reconstruct a tomographic image from the gated projection data using an iterative reconstruction method including a regularization term and using the weighting-and-feathering coefficients.

To overcome the problems of the related art, a method of iterative reconstruction (IR) using weighted projection data can be used to reconstruct tomographic images from gated projection data. These reconstructed images have several improvements over conventional reconstruction methods, including improved signal to noise ratio (SNR), minimization of banding artifacts, and minimization of low-frequency shading artifacts. In certain embodiments, the method includes feathering the transitions between gated and not gated projection data by using a smooth transition function (e.g., a continuously differentiable function). Further, in certain embodiments, the method includes that the projection data is weighted to create uniform data redundancy throughout the sampled volume. Furthermore, in certain embodiments, the iterative image reconstruction method includes minimizing a cost function including a regularization term that can be, e.g., a total-variation (TV) minimization regularization term.

Figure 1:
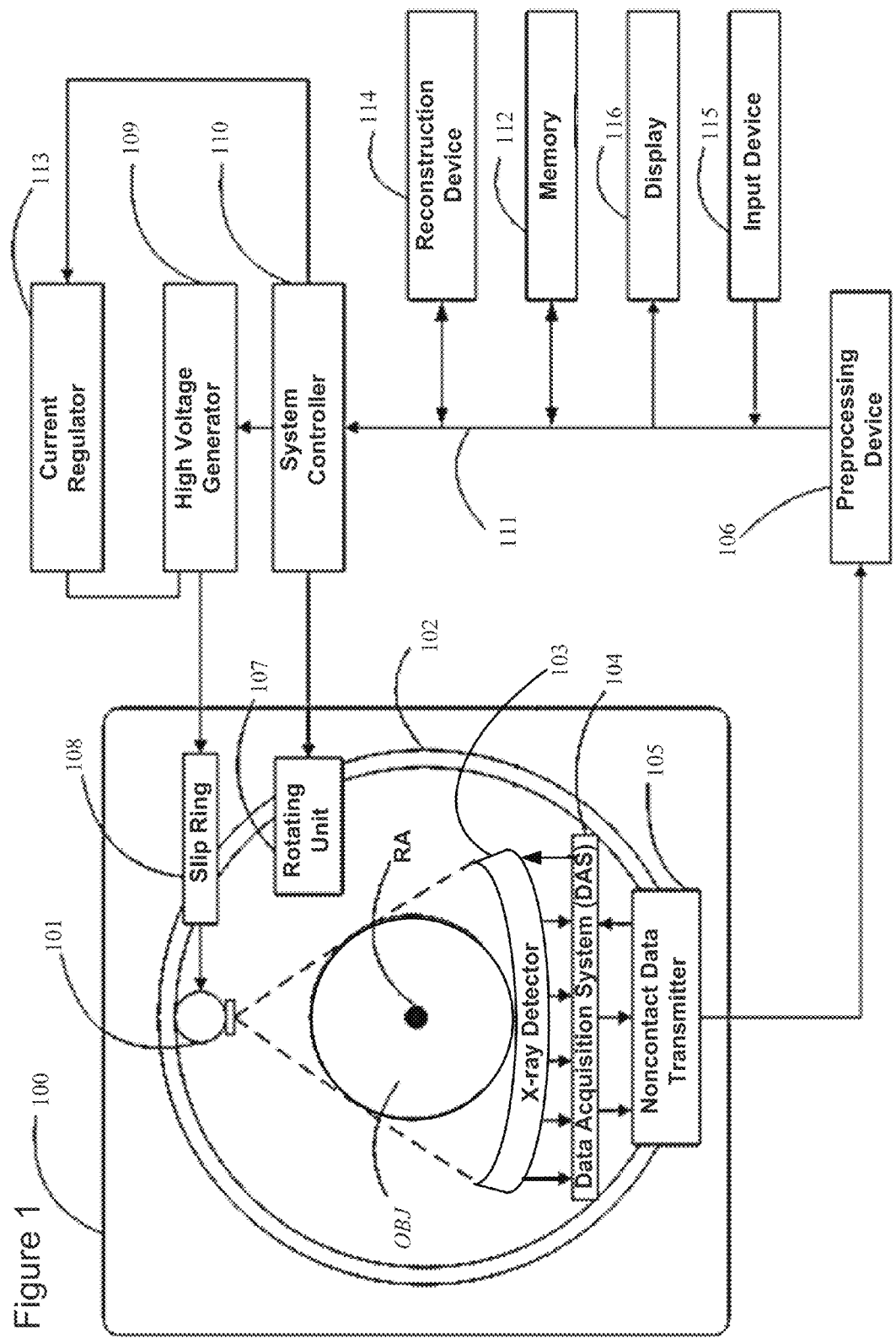
FIG. 1 shows a schematic drawing of one implementation of a CT apparatus having a source and detectors for measuring CT projection data.

Referring now to the drawings, wherein like reference numerals designate identical or corresponding parts throughout the several views, FIG. 1 illustrates an implementation of a radiography gantry included in a CT apparatus or scanner. As shown in FIG. 1, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating apparatus 107 rotates the annular frame 102 at a high speed, such as 0.4 sec/rotation, while the object OBJ is being moved longitudinally along the axis RA into or out of the illustrated page.

Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high-voltage generator 109 that generates a tube voltage applied to the X-ray tube 101 through a slip ring 108 so that the X-ray tube 101 generates X-rays. The X-rays are emitted towards the object OBJ, whose cross sectional area is represented by a circle. The X-ray detector 103 is located at an opposite side from the X-ray tube 101 across the object OBJ for detecting the emitted X-rays that have been transmitted through the object OBJ. The X-ray detector 103 further includes individual detector elements or modules.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 800 TPPR, 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data, at a stage immediately before reconstruction processing. The memory 112 is connected to a system controller 110 through a data/control bus 111, together with a reconstruction device 114, input device 115, and display 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The memory 112 can store the measurement value representative of the irradiance of the X-rays at the X-ray detector unit 103. Further, the memory 112 can store a dedicated program that executes, e.g., the CT image reconstruction method 300 discussed herein.

The reconstruction device 114 can execute the CT image reconstruction method 300 discussed herein. Further, reconstruction device 114 can execute pre-reconstruction processing image processing such as volume rendering processing and image difference processing as needed. The pre-reconstruction processing of the projection data performed by the preprocessing device 106 can include correcting for detector calibrations, detector nonlinearities, polar effects, noise balancing, and material decomposition. Post-reconstruction processing performed by the reconstruction device 114 can include filtering and smoothing the image, volume rendering processing, and image difference processing as needed. The image reconstruction process can be performed using filtered back-projection (FBP), iterative image reconstruction methods, or stochastic image reconstruction methods. The reconstruction device 114 can use the memory 112 to store, e.g., projection data, reconstructed images, calibration data and parameters, and computer programs.

The reconstruction device 114 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 112 can be non-volatile, such as ROM, EPROM, EEPROM or FLASH memory. The memory 112 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 116. The display 116 can be an LCD display, CRT display, plasma display, OLED, LED or any other display known in the art.

The memory 112 can be a hard disk drive, CD-ROM drive, DVD drive, FLASH drive, RAM, ROM or any other electronic storage known in the art.

Figure 2A:
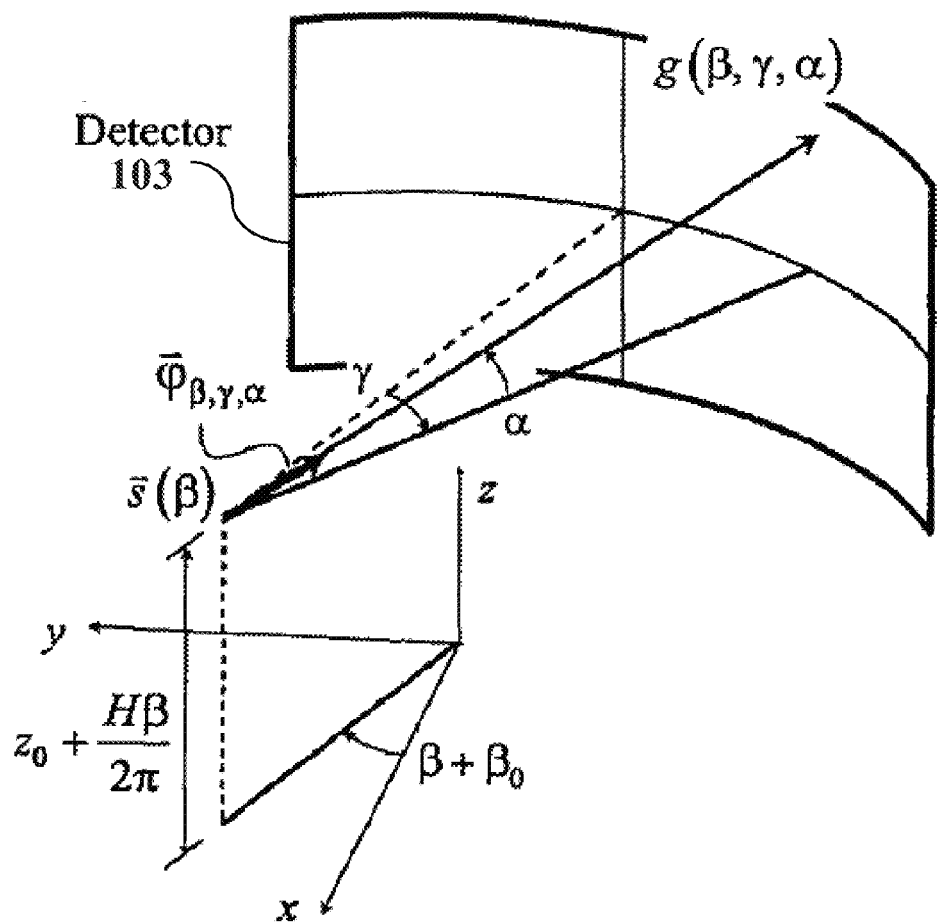
FIG. 2A shows a diagram of a ray from an X-ray beam incident on a detector and nomenclature describing the focus location, the projection angle of the beam, and the angle of a ray within the beam.

FIG. 2A shows a cone-beam geometry of a ray from the X-ray tube 101 to the X-ray detector 103. In general, the projective measurements of the rays can be expressed as the line integral $$g(\beta,\gamma,\alpha)=\int_0^\infty f(s(\beta)+l\phi_{\beta,\gamma,\alpha})dl,$$

$$s(\beta)=[R\cos(\beta+\beta_0), R\sin(\beta+\beta_0), z_0+H\beta/2\pi]^T,$$

where f(r) is the object to reconstruct, R is the radius of the helical orbit, H is the helical pitch (table feed per rotation), $(\beta,\gamma,\alpha)$ denote projection, ray, and cone angle, respectively (see FIG. 1), and $\phi_{\beta,\gamma,\alpha}$ denotes the unit vector directed from the X-ray focus $s(\beta)$ toward the point $(\gamma,\alpha)$ on the cylindrical detector surface at $\beta$, where $$\phi_{\beta,\gamma,\alpha}=[-\cos(\beta+\beta_0+\gamma)\cos\alpha, -\sin(\beta+\beta_0+\gamma)\cos\alpha, \sin\alpha]^T.$$

At $\beta=0$, the focus is in the plane of interest $z=z_0$ at projection $\beta_0$.

Figure 2B:
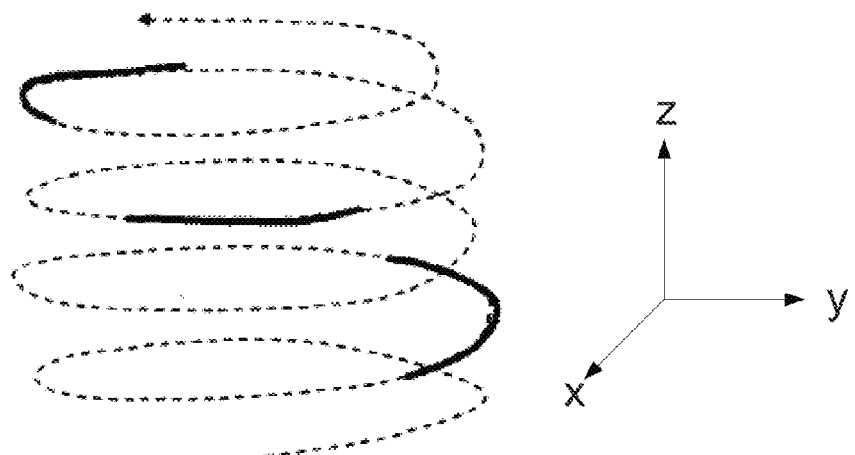
FIG. 2B shows an example of a helical path of an X-ray source around an imaged object.

FIG. 2B shows an example of a helical path of the X-ray tube about the imaged object OBJ. In certain implementations, the object OBJ will be placed on a table that is translated linearly as the X-ray tube 101 and X-ray detector 103 are rotated along respective circular paths, such that the path of the X-ray-tube 101 traverses a helical path relative to the object OBJ. In certain implementations, the projection angle β is related to the variables time t and position z by the expressions $$t/T_{rot} = \beta/2\pi = (z+z_0)/H$$

so that t=β=0 when the source is at the slice of interest $z_0$.

The dashed line in FIG. 2A shows the helical path of the X-ray source (e.g., the X-ray tube 101) relative to the imaged object OBJ. The solid lines exemplify an ECG gating scenario, wherein the solid lines indicate the subset of X-ray tube locations corresponding to gate signals, such as those that can be obtained from an electrocardiographic gate signal shown in FIG. 4. In certain implementations, the gated projection data might not span all of the projection angles. Even when the gated projection data do not span all of the projection angles, a reconstructed image can be reconstructed from the gated projection data when certain predefined conditions (e.g., Tuy's condition discussed later) are satisfied.

In one implementation, projection data is acquired without translating the imaged object OBJ relative to the X-ray tube 101 and X-ray detector 103. This scenario of circular (as opposed to helical) trajectories results in simplifying the analysis by setting H=0. The nomenclature for the ray shown in FIG. 2A is generally applicable to all X-ray beams including cone beams and fan beams. In a fan beam geometry (e.g., a parallel fan beam wherein the X-rays are divergent in one dimension and collimated in another dimension), the analysis can be simplified by setting α=0.

Figure 3:
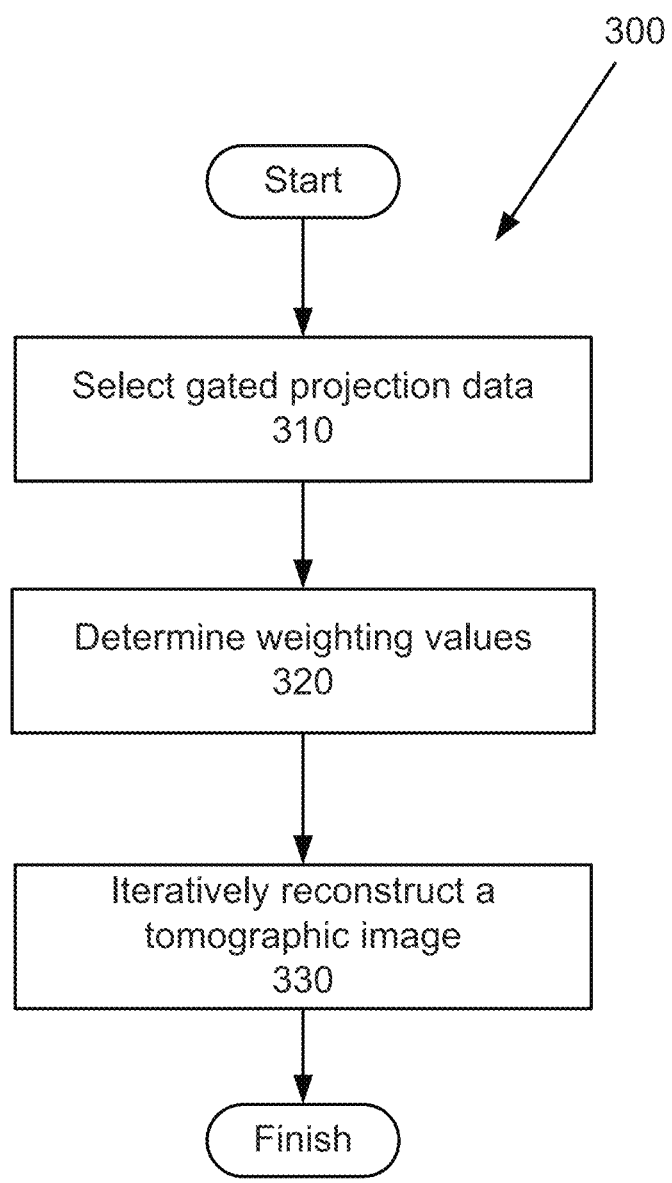
FIG. 3 shows an example of a method of reconstructing a tomographic image from gated projection data.

FIG. 3 shows a flow diagram of a method 300 of reconstructing tomographic images by gating projection data according to a gate signal.

Figure 4:
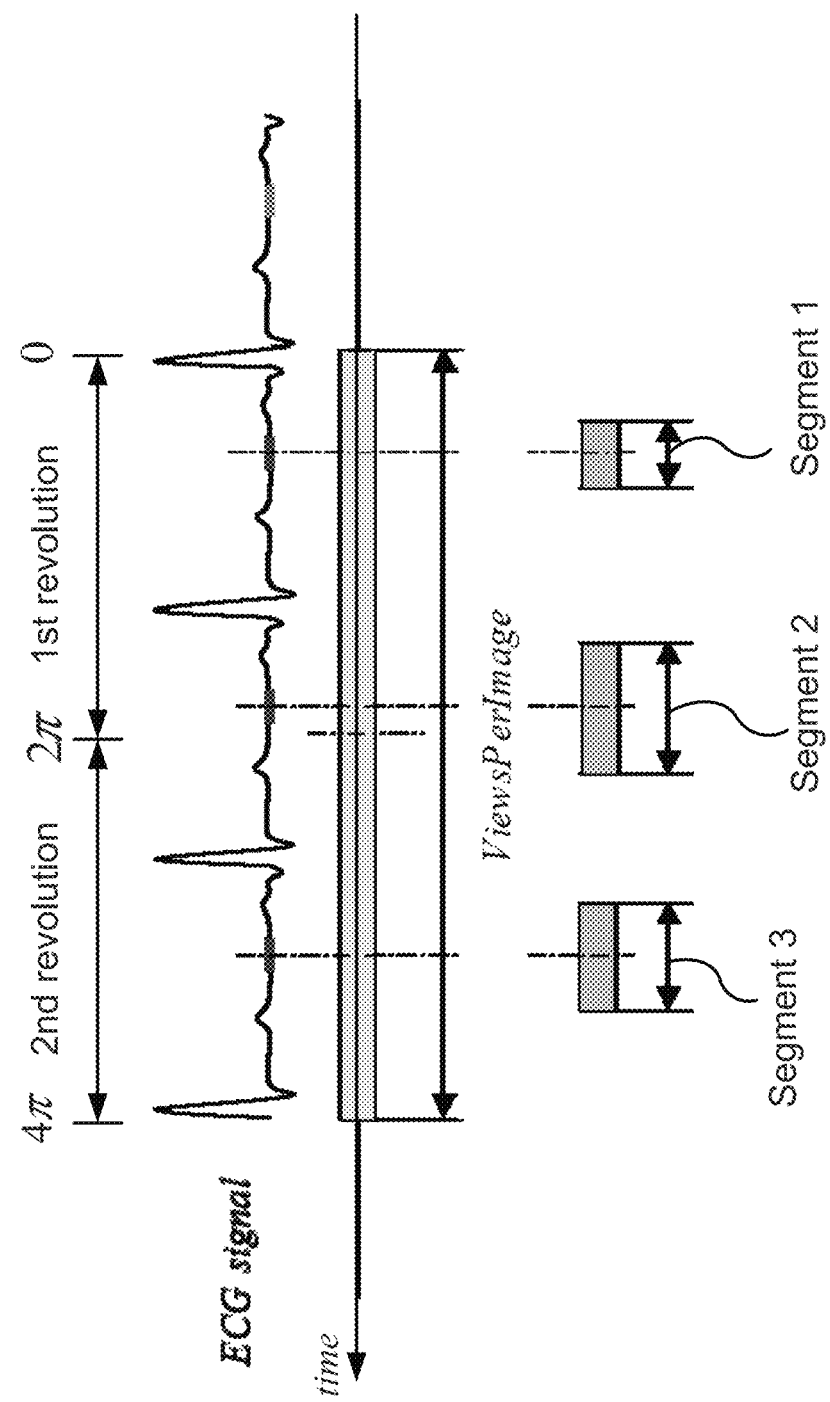
FIG. 4 shows one implementation of an electrocardiographic signal used to gate segments of projection data to be used for reconstruction of a tomographic image.

The first step 310 of method 300 is selecting gated projection data. FIG. 4 shows an example of an ECG signal. Below the ECG signal, a band shows an example of a time during which two complete revolutions of projection data are acquired. The first revolution is depicted as spanning from 0 to 2π, and the second revolution is depicted as spanning from 2π to 4π. During the period of each heartbeat, a portion of the heartbeat is selected as the gate signal—the bold sections of the ECG signal in FIG. 4. Using these gate signals, a subset of projection data corresponding to the gate signals is selected as gated projection data. FIG. 2A shows another example of gated projection data for a helical scan. In FIG. 2A, the position of the X-ray source is plotted relative to the object OBJ as a dashed line and the gated projection data is indicated by a solid line.

The width of each segment (i.e., a subset of continuous projection data) can depend on various factors, including: the shape of the ECG signal, the heart rate, and whether the image is systole, diastole, or another portion of the cardiac cycle, for example. Selecting a narrower subset of projection angles around the gate signals improves the temporal resolution of the reconstructed images, assuming minimal changes between heartbeats.

On the other hand, increasing the width of each segment enables spanning the minimal coverage of projection angles in fewer heartbeats. When the period of the heartbeat and the revolution period of the CT apparatus are different, subsequent CT revolutions will include gated projection angles not previously sampled. Therefore, each scan increases the projection-angle span of the gated projection data, such that repeated scans/rotations of the CT apparatus will eventually result in the gated projection data satisfying the minimal coverage of projection angles. If the number of rotations is large, then the risk of movement between at least one of the CT revolutions will also be large. To minimize the risk of movement between CT revolutions, the number of CT revolutions should be kept small. In certain implementations, the number of revolutions required to achieve the minimum coverage can be decreased by increasing the span of projection angles corresponding to each gate signal. However, increasing the span of projection angles corresponding to each gate signal also has the consequence of decreasing temporal resolution.

Figure 5:
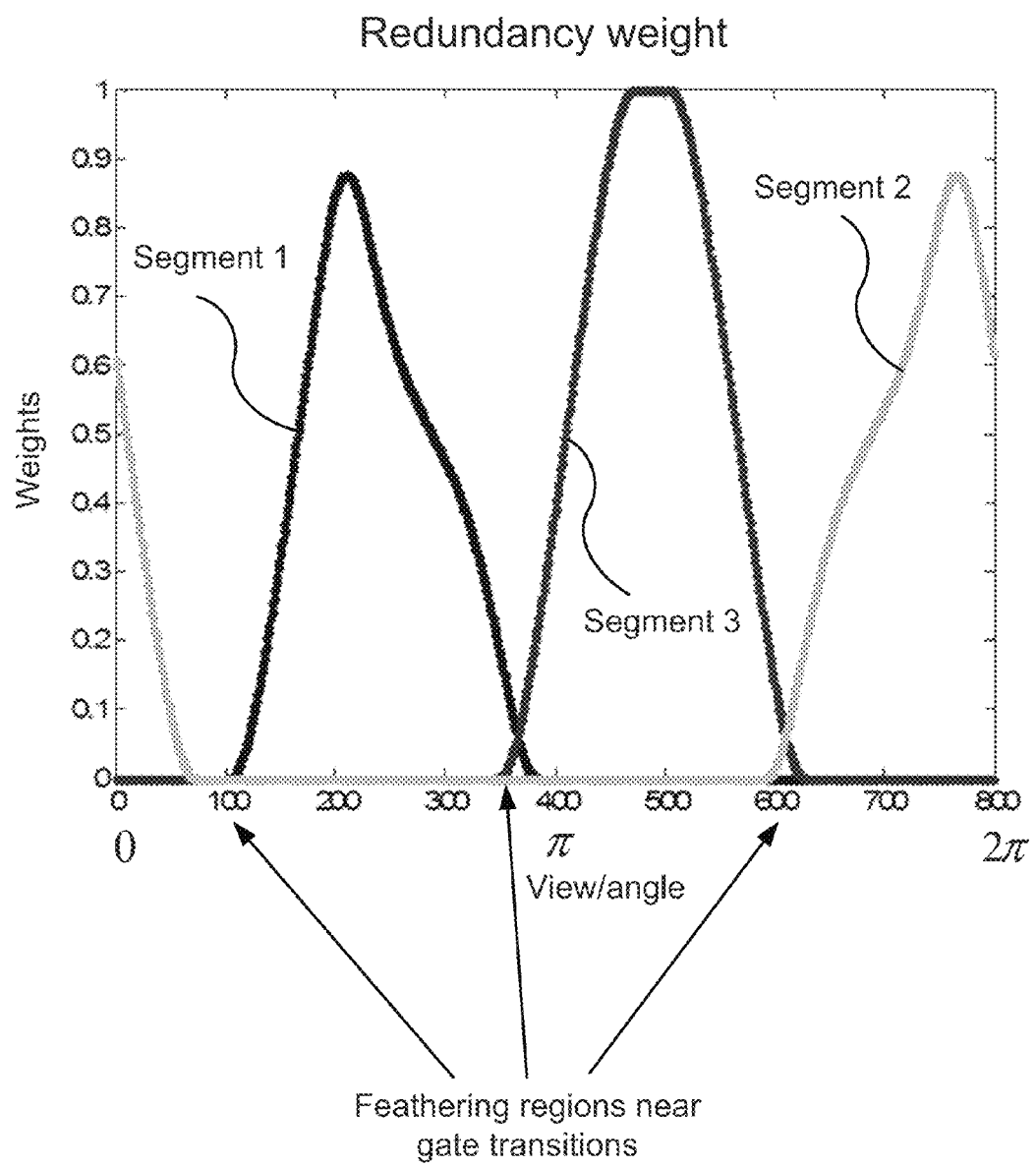
FIG. 5 shows a one implementation of weighting values applied to segments of projection data to be used for reconstruction of a tomographic image.

In the second step 320 of method 300, the weight values for the gated projection data are determined. FIG. 5 shows an example of weight values that can be applied to the three gated segments shown in FIG. 4. These weight values, shown in FIG. 5, are for the central slice of a cone-beam for a circular scan (i.e., not a helical scan). In FIG. 5, one revolution corresponds to 800 views (i.e., 800 projection angles per revolution), which are plotted along the horizontal axis. Also shown along the horizontal axis—below the view number—is the projection angle β given in radians. The third segment occurs during the second revolution, and is plotted superimposed on the first and second segments by taking the modulo 2π of the projection angle.

Using weight values such as those shown in FIG. 5 has several advantages over weighting each projection angle equally. When all of the gated projection data is weighted equally, certain artifacts are manifest in the reconstructed image. These artifacts can be mitigated by weighting the projection data according to predefined criteria. For example, by feathering the gated projection data at the edges of each segment, the banding artifacts can be mitigated. Feathering refers to replacing abrupt transitions at the edges of each segment with a smooth transition, such as the smooth transitions shown in FIG. 5 in the feathering regions. Smooth transition include, e.g., continuously differentiable functions.

Figure 6:
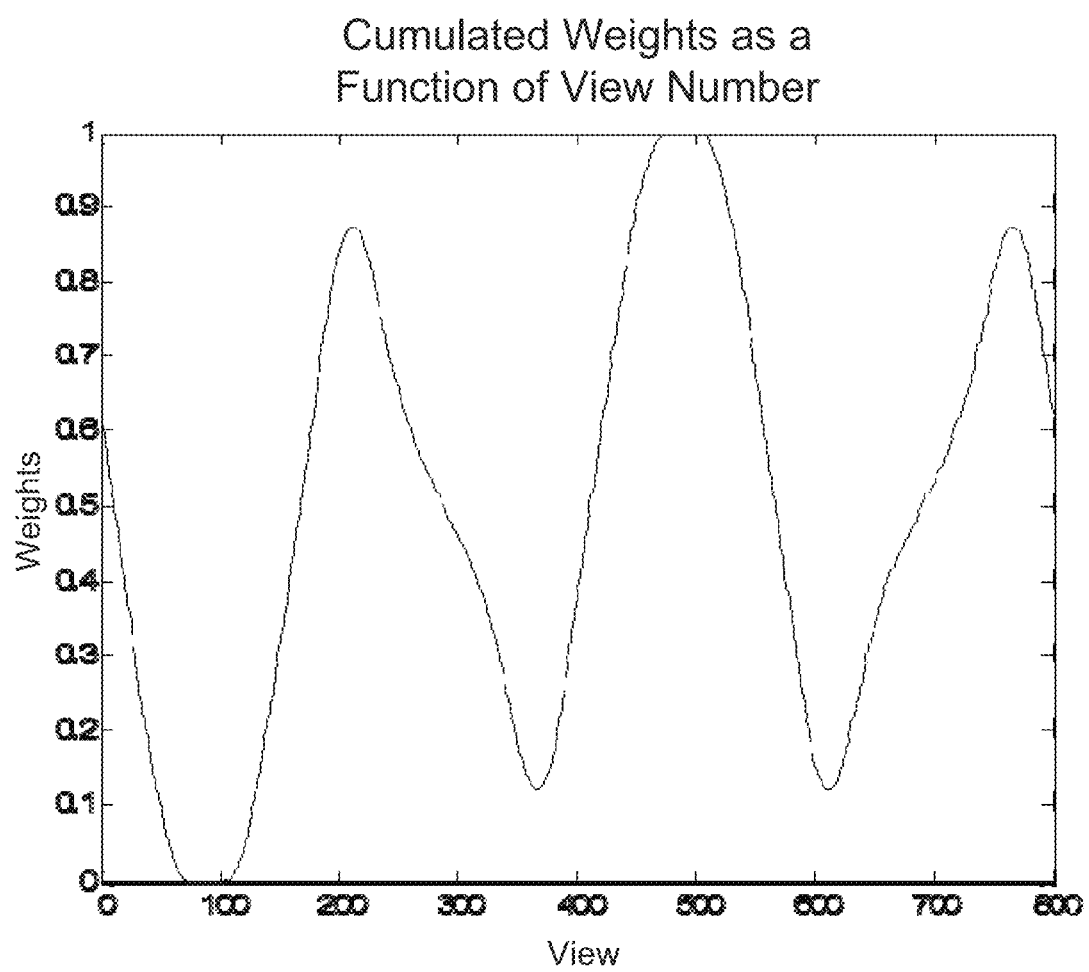
FIG. 6 shows a one implementation of summing weighting values from different projection-data segments corresponding to common view angles.
Figure 7:
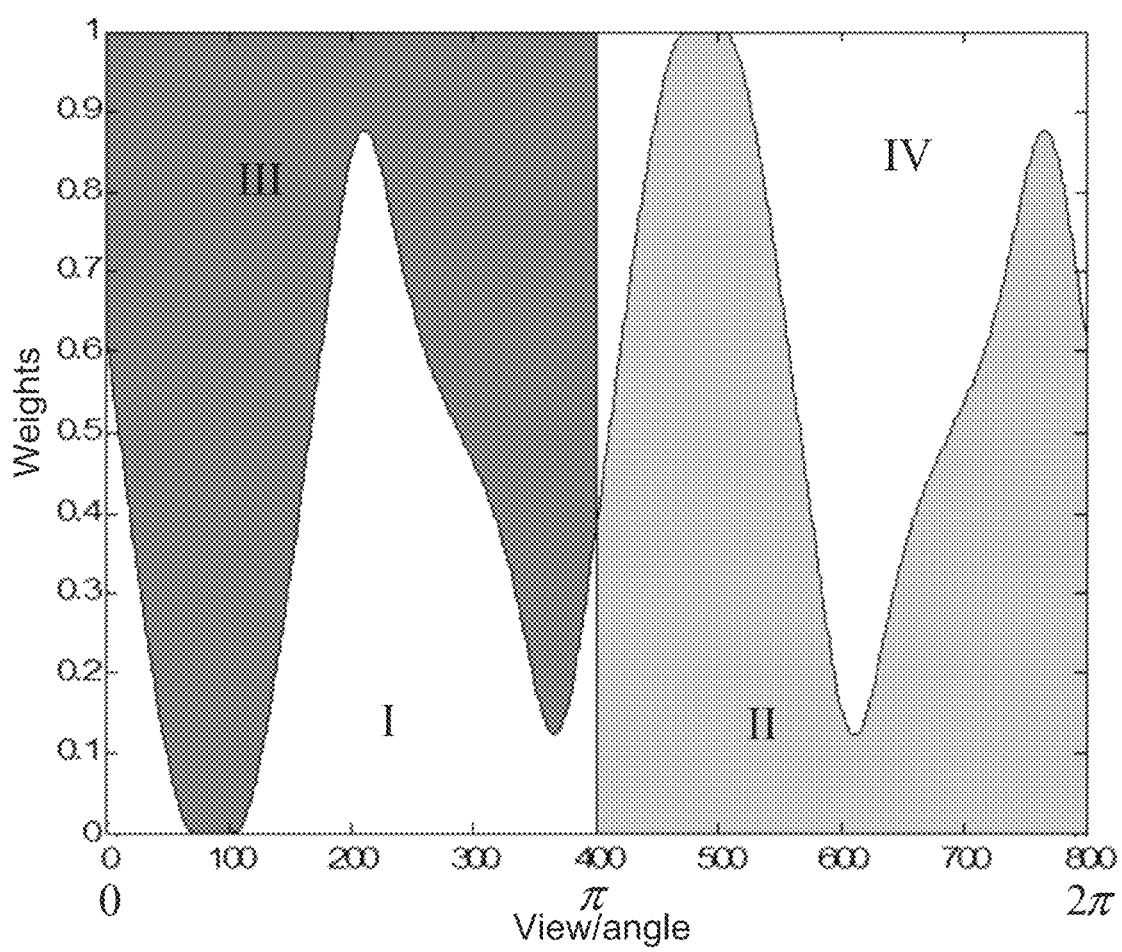
FIG. 7 shows a symmetry of the sum of weighting values, wherein the symmetry exemplifies one method of compensating for unequal data redundancy in the gated projection data.

A second aspect of the weighting values is correcting for unequal sampling of the imaged object due to uneven data redundancy resulting from the statistical and uncontrolled qualities of the gate signals (e.g., variations in the heart rate). How the unequal data redundancy is corrected can be observed in the symmetry of the weighting values. FIG. 6 shows the superposition of the weighting values for the segments plotted of FIG. 5. These weighting values exhibit a symmetry resulting from the fact that the weight values equilibrate the data redundancy according to which views sample which portions of the imaged object OBJ. FIG. 7 shows this symmetry more clearly, wherein four regions (i.e., regions I, II, III, and IV) are identified. When region I and region II are overlaid and summed, the two regions add to a constant value of one (i.e., if region II were reflected vertically, it would be identical to region III). This symmetry is an example of compensating correcting for inequalities in the data redundancy by increasing the weighting of certain projection angles to compensate for the underrepresentation of other symmetrically opposed projection angles.

The weighting scheme shown in FIG. 5 is not the only possible weighting scheme. For example, compensating for unequal data redundancy is often discussed in the context of short-scan FBP reconstruction methods. As discussed in U.S. Pat. No. 7,751,524, incorporated herein by reference in its entirety, and discussed in U.S. Pat. No. 6,907,100, incorporated herein by reference in its entirety, image reconstruction for short-scan cone-beam (CB) CT can be performed using a method similar to the FBP method for full-scan CB CT, with a difference being that the projection data for short-scan CT are weighted according to the projection angle. This weighting of the projection data corrects for the unequal data redundancy of the short-scan data. For example, the Parker weights, among others, can be used for a half-scan (i.e., a scan of 180°+2γ, where γ is the half fan angle).

In one implementation, the Feldkamp method is used to reconstruct images from CB CT projection data. In the Feldkamp method, a convolution-backprojection formula is used for direct reconstruction of a three-dimensional density function from a set of two-dimensional projections. Feldkamp's approach was derived as a heuristic generalization of the classical two-dimensional fan-beam reconstruction method. The early 1980s brought some significant breakthroughs in the analytical CB reconstruction theory. Advancements were mainly driven by the contributions of Tuy, Smith, and in particular by that of Grangeat.

One important issue in the context of three-dimensional CB image reconstruction is the question under which circumstances accurate reconstruction of the image f is possible. Among several contributions to this issue, Tuy's formulation of the CB data sufficiency criterion has gained the most attention. Tuy's sufficiency criterion states that theoretically-exact and stable CB reconstruction at a point (x,y,z) is possible, if and only if almost every plane through (x,y,z) has at least one intersection with the source trajectory.

Numerical algorithms for accurate CB reconstruction from data that satisfies Tuy's sufficiency condition can be composed by a direct implementation of, e.g., the Feldkamp method discussed above with the modifications developed by Grangeat. Applying the Grangeat formulation to each acquired CB projection successively delivers the intermediate Radon function throughout the three-dimensional Radon domain.

Subsequent research was focused on deriving CB reconstruction algorithms that follow the practical FBP scheme, where every CB projection can be processed immediately after it has been measured. Clack and Defrise and also Kudo and Saito both suggested schemes to find such FBP-type CB reconstruction algorithms for a variety of source trajectories. One important ingredient in these schemes is a weighting function, which needs to be adapted to the considered source trajectory, and accounts for redundancies in the intermediate Radon function that can be obtained from the given CB data set. The resulting numerical CB reconstruction algorithms are based on a shift-variant filtering step and a subsequent three-dimensional weighted CB backprojection of the filtered data; these FBP methods allow accurate reconstruction, as long as the considered CB data is non-truncated and also satisfies Tuy's sufficiency condition. Additionally, it has been shown that the application of these schemes to a full circular source trajectory yields an algorithm that coincides with the one suggested by Feldkamp, thus setting that heuristically derived method into a firm theoretical framework.

Another breakthrough in CB reconstruction theory was achieved by Katsevich, who suggested a novel general scheme to derive image reconstruction algorithms for theoretically-exact reconstruction from CB data that satisfies Tuy's sufficiency condition. This scheme is related to the ones described in the previous paragraph, which also requires a proper definition of a redundancy weighting function to find a practical algorithm for a given source trajectory. In contrast, Katsevich's method enables the composition of FBP algorithms for many practically relevant scenarios. These FBP algorithms achieve data filtering by a shift-invariant one-dimensional convolution along specific filter directions. Therefore, these FBP algorithms are more efficient than conventional algorithms and, in general, more flexible with respect to truncation in the CB data, depending on the required filter directions. In recent years, a variety of attractive reconstruction algorithms have been derived from Katsevich's general theory, including: helical source trajectories, circle-plus-arc trajectories, and the ellipse-plus-oblique-line trajectory, to name only a few.

In general, the short-scan reconstruction and weighting schemes discussed above can be generalized to be compatible with the gating method described in reference to FIG. 4. In this way the naturally occurring unequal data redundancy of gated projection data can be accounted for and corrected.

Additionally, as discussed in U.S. patent application Ser. No. 11/094,468, incorporated herein by reference in its entirety, the Taguchi weights can also be used to account for and correct data redundancy. For example, Taguchi discloses that, for a cone beam, an image can be reconstructed using the expression $$f(x, y, z) = \frac{R}{2\pi} \int_{-\beta_m}^{\beta_m} \frac{1}{L(x, y, \beta)^2} \int_{-\gamma_m}^{\gamma_m} \{h(\gamma - \gamma')[wn(\beta, \gamma', \alpha)g(\beta, \gamma', \alpha)]\}d\gamma' d\beta,$$

wherein $\beta_m$ and $\gamma_m$ are limits to the integration angles, $wn(\beta,\gamma,\alpha)$ are the weight values, $g(\beta,\gamma,\alpha)$ are the projection data, $h(\gamma-\gamma')$ is a filter function (e.g., a ramp filter, Ram-Lak filter, or Shepp-Logan filter), R is the radius of the orbit, and $L(x,y,\beta)$ refers to the distance from the focus at $\beta$ to a pixel at (x,y). In discretized form, the above integral can be expressed as a matrix equation $$f = A^{-1}g,$$

wherein $A^{-1}$ is the back-projection matrix (which is the inverse of the forward-projection matrix of A), and $A^{-1}$ can be calculated directly using the above integral rather than calculating the inverse matrix of A. Improved image quality of the reconstructed image can be achieved when certain conditions are satisfied (e.g., Tuy's sufficiency condition). Additionally, for a cone-beam reconstruction, the weighting values wn should satisfy $$\sum_{j=-J}^{J} wn(\beta_{c(j)}, \gamma_{c(j)}, \alpha_{c(j)}) = 1; \ j \in \text{integer},$$

wherein $$\beta_{c(n)} = \begin{cases} \beta + n\pi + 2\gamma & (n = \text{odd}) \\ \beta + n\pi & (n = \text{even}) \end{cases},$$

$$\gamma_{c(n)} = \begin{cases} -\gamma & (n = \text{odd}) \\ \gamma & (n = \text{even}) \end{cases},$$

$$\alpha_{c(n)} = \tan^{-1}(-H\beta_{c(n)}/2\pi L_{c(n)}),$$

$$L_{c(n)} = \begin{cases} 2R\cos\gamma - L & (n = \text{odd}) \\ L & (n = \text{even}) \end{cases},$$

$$L = -H\beta/2\pi \tan\alpha, \text{ and}$$

$$H\beta_{c(n)}/2\pi = (z_0 - z(\beta_{c(n)}))/\tan\alpha.$$

The Taguchi weighting method discussed herein uses helical scanning as an example. However, this is in no way limiting and the choice of the scanning mode or orbit is arbitrary. For example, the Taguchi weighting method could also be used with a continuous circular scan ($\beta > 2\pi$). For a circular scan, the above expression can be simplified by setting H=0.

According to one embodiment, the weight values can be determined by applying a feathering technique to the edges of each segment. Consider, for example, the case wherein the gated segments of projection data are equally spaced, each having an equal width in projection angles (e.g., where a first segment spans 0° to 60°, a second segment spans 120° to 180°, and a third segment spans 240° to 300°). These symmetric segments can be referred to as patches. Several examples of feathering are discussed herein using the non-limiting example of patches.

For example, each patch can transition using a smooth function. One defines a time window, or "patch," centering each gating point with a certain width in time t (thus, in projection angle $\beta$, wherein time t and projection angle $\beta$ are related by the previously described relation). Let Npatch denote the number of patches within $2\beta_m$, wherein $2\beta_m$ is the data range used for reconstructing the image, and let ip be the patch index from 0 to Npatch-1. A cardiac time window function $c(ip, \beta)$ can be defined for each $ip^{th}$ patch. The symmetric time window function is centered at the gating point $t_{gt}(ip)$ with width $2t_{sz}(ip)$. In terms of projection angle, the gating point is defined as $\beta_{gt}(ip)$ and the window width $\lambda\beta_{sz}(ip)$. A nonzero value of $c(ip,\beta)$ indicates $\beta$ is inside of the patch ip.

In two-dimensional image reconstructions, when conditions D-1 and D-2 are satisfied, an exact reconstruction can be performed by the weighted FBP with a ramp filtering even if projections (patches) are disconnected with respect to $\beta'$ where $\beta'=\mod(\beta,2\pi)$. The conditions are: (D-1) all 2D ray-sums through the object are obtained at least once as either primary or complementary rays; and (D-2) the weights normalize the redundancy of the samples and are smooth enough to avoid a numerical error in filtering step; where the primary ray is the ray of interest while the complementary ray refers to the one whose projected path onto the xy plane coincides with that of the primary ray.

In one implementation, the cardiac time window function can be defined as $$c(ip, \beta) = \begin{cases} 0 & \text{if } \beta < \beta s(ip) \\ \text{rising}[(\beta - \beta s(ip))/\beta_f] & \text{if } \beta s(ip) \leq \beta \leq \beta s(ip) + \beta_f \\ 1 & \text{if } \beta s(ip) + \beta_f \leq \beta \leq \beta e(ip) - \beta_f \\ \text{rising}[(\beta e(ip) - \beta)/\beta_f] & \text{if } \beta e(ip) - \beta_f \leq \beta \leq \beta e(ip) \\ 0 & \text{if } \beta e(ip) < \beta \end{cases}$$

$$\text{rising}(x) = \begin{cases} 0 & \text{if } x \leq 0 \\ 3x^2 - 2x^3 & \text{if } 0 < x < 1 \\ 1 & \text{if } x \geq 1 \end{cases}$$

wherein $\beta s$ (ip) and $\beta e(ip)$ are the angles corresponding to the beginning and the end of segment ip, respectively, and $\beta_f$ is the feathering angular range.

Alternatively, in three dimensions, one may use:

$$c(ip, \beta, \alpha) = \begin{cases} 0 & \text{if } \beta < \beta s(ip) \\ \text{triangle}(\alpha/\alpha_m) \times \\ \text{rising}[(\beta - \beta s(ip))/\beta_f] & \text{if } \beta s(ip) \leq \beta \leq \beta s(ip) + \beta_f \\ \text{triangle}(\alpha/\alpha_m) & \text{if } \beta s(ip) + \beta_f \leq \beta \leq \beta e(ip) - \beta_f , \\ \text{triangle}(\alpha/\alpha_m) \times \\ \text{rising}[(\beta e(ip) - \beta)/\beta_f] & \text{if } \beta e(ip) - \beta_f \leq \beta \leq \beta e(ip) \\ 0 & \text{if } \beta e(ip) < \beta \end{cases}$$

wherein $$\text{triangle}(x) = \begin{cases} 1 - |x| & \text{if } |x| \leq 1 \\ 0 & \text{otherwise} \end{cases}.$$

Moreover, the triangle function used therein is only an example; for instance, a Gaussian, trapezoid, or other function could also be used. The normalized weight are then calculated using $$wn(\beta, \gamma, \alpha) = \frac{\sum_{ip}^{Npatch-1} c(ip, \beta, \alpha)}{\sum_{ip}^{Npatch-1} \sum_{j=-\infty}^{\infty} c(ip, \beta_{c(j)}, \alpha_{c(j)})}$$

In another implementation, a trapezoid function that can also be used for feathering. For example, a trapezoid function can be defined as $$\text{trapezoid}(x, a) = \begin{cases} 1 & \text{if } |x| \leq a \\ 0 & \text{if } |x| \geq 1 \\ 1 - \frac{x-a}{1-a} & \text{otherwise} \end{cases}$$

The weight and width of each patch can be adjusted to satisfy the coverage (D-1) and the data redundancy (D-2) criteria. For example, the "ratios" of each patch in size and weight can then be independently defined by $w\text{Weight}(ip)=\text{trapezoid}(|,\beta_p(ip)-\beta_0|/\beta w,aw)$ and $w\text{Size}(ip)=\text{trapezoid}(|\beta_p(ip)-\beta s,as)$ wherein $\beta w$ is the widths of the bottom of the trapezoid function along $\beta$-axis, respectively; aw and as are parameters that define the breaking point (or the shoulder of the flat region in the trapezoid), respectively; and $\beta_p(ip)$ is the projection angle for which the focal spot is at the center of segment ip. Then, let the sizes of a plurality of patches contributing to the reconstruction of a slice be wSize(ip): wSize(ip+1): wSize(ip+2): . . . . This can be achieved by starting a zero-width patch at each gating point, adjusting the patch expansion increment to the ratio above, and repeating the iterative patch expansion until the minimum coverage or Tuy's sufficiency condition is satisfied.

For a cone-beam geometry, the normalized weight values are then given by $$wn(\beta, \gamma, \alpha) = \frac{\sum_{ip}^{Npatch-1} wWeight(ip) \times c(ip, \beta, \alpha)}{\sum_{ip}^{Npatch-1} \sum_{j=-\infty}^{\infty} wWeight(ip) \times c(ip, \beta_{c(j)}, \alpha_{c(j)})}.$$

Similarly, for a fan-beam geometry, the normalized weight values are then given by $$wn(\beta, \gamma) = \frac{\sum_{ip}^{Npatch-1} wWeight(ip) \times c(ip, \beta)}{\sum_{ip}^{Npatch-1} \sum_{j=-\infty}^{\infty} wWeight(ip) \times c(ip, \beta_{c(j)})}.$$

As can be seen by the above discussion, there are many methods for determining weighting values to account for and correct unequal data redundancy. Conventionally, these weighting schemes have been applied to FBP reconstruction methods. One of ordinary skill in the art will recognize that many different feathering functions and weighting values can be used to reconstruct a tomographic image. Generally, the feathering functions should provide a smooth transition at the edges of the gated segments of projection data. Further, the weighting functions should account for and equilibrate unequal data redundancy within the gated projection data.

The third step 330 of method 300 is reconstructing the tomographic image using an IR method. In one implementation, the image reconstruction problem can be recast into a cost-function minimization problem, wherein the cost function is expressed as $$C(f) = \|g - Af\|_W^2 RT(f),$$

wherein g=A f is the system matrix equation for the CT projection measurements, as discussed above, and RT (f) is a regularization term. The notation $\|x\|_W^2$ signifies a weighted inner product of the form $x^T W x$. The choice of regularization term can be based on the details of the imaging problem. The regularization term can be one of a negative absorption constraint (e.g., projection on convex sets (POCS)), a quadratic regularization, an edge-preserving regularization (e.g., a Gaussian Markov Random Field regularization or a total-variation (TV) minimization regularization).

The cost function minimization problem can be expressed as solving for the argument f that minimizes the cost function:

$$\underset{f}{\operatorname{argmin}} C(f) = (Af - g)^T W(Af - g) - RT(f).$$

In one implementation, the weight matrix W is a statistical weighting matrix representing the uncertainty of the respective projection data (e.g., the standard deviation of the measured irradiance at each pixel). When the noise on each pixel is uncorrelated with the other pixels and projection angles, the statistical weighting matrix will be diagonal. On the other hand, when the noise in the projection data is correlated, the statistical weighting matrix becomes non-diagonal. A statistical weighting matrix that is non-diagonal can be diagonalized, e.g., by setting the off-diagonal terms to zero. By replacing the non-diagonal statistical matrices with the diagonal matrix, the optimization problem is converted from a maximum-likelihood problem to a least-squares problem. In exchange for giving up the better image quality of the maximum a posteriori (MAP) solution, the least-squares formulation will normally converge faster than the MAP formulation when using the conventional iterative optimization methods.

In one implementation, the weight matrix W represents the data redundancy weighting values $wn(\beta,\gamma,\alpha)$. For example, the weight matrix W can be a diagonal matrix with the respective weighting values $wn(\beta,\gamma,\alpha)$ corresponding to the gated projection data along the diagonal.

In one implementation, the weight matrix W represents a product of a redundancy weighting matrix and a statistical weighting matrix.

There are many methods of minimizing the cost function. For example, the cost function could be minimized using any known multi-dimensional minimization method, such as a gradient descent method, a Levenberg-Marquardt method, a Nedler-Mead method, Gauss-Newton method, etc. Additionally, the cost function can be minimized using one of the conventional primal-dual algorithms. These conventional primal-dual algorithms include: the forward-backward proximal splitting method, the Douglas-Rachford splitting method, the alternating direction method of multipliers, the Korpelevich extragradient method, the Arrow-Hurwicz method, the Nesterov's smoothing method, and the Chambolle-Pock primal-dual. The minimization problem can also be solved using an augmented Lagrangian multiplier method.

After completing step 330 of method 300, the argument corresponding to the minimum of the cost function is the reconstructed image. The reconstructed image is then post-processed using image processing and volume rendering methods to intuitively present the information from the image to a user. Additionally, the reconstructed image can be stored for later use.

Figure 8A:
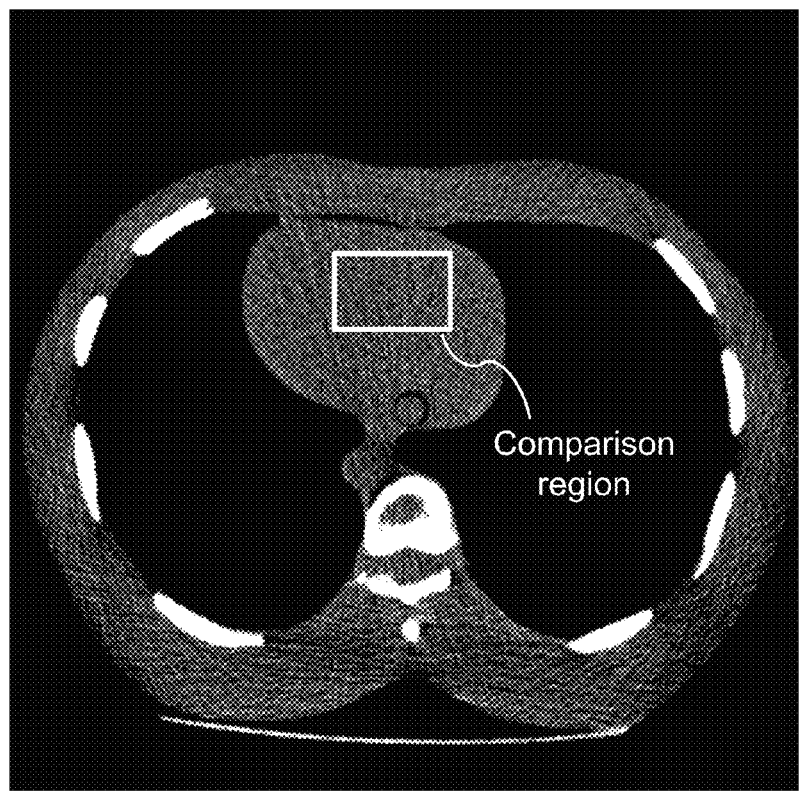
FIG. 8A shows an example of a reconstructed XY-plane image from weighted and gated projection data using a filtered back-projection (FBP) method, wherein the image is slice number 160 of 320 slices.
Figure 8B:
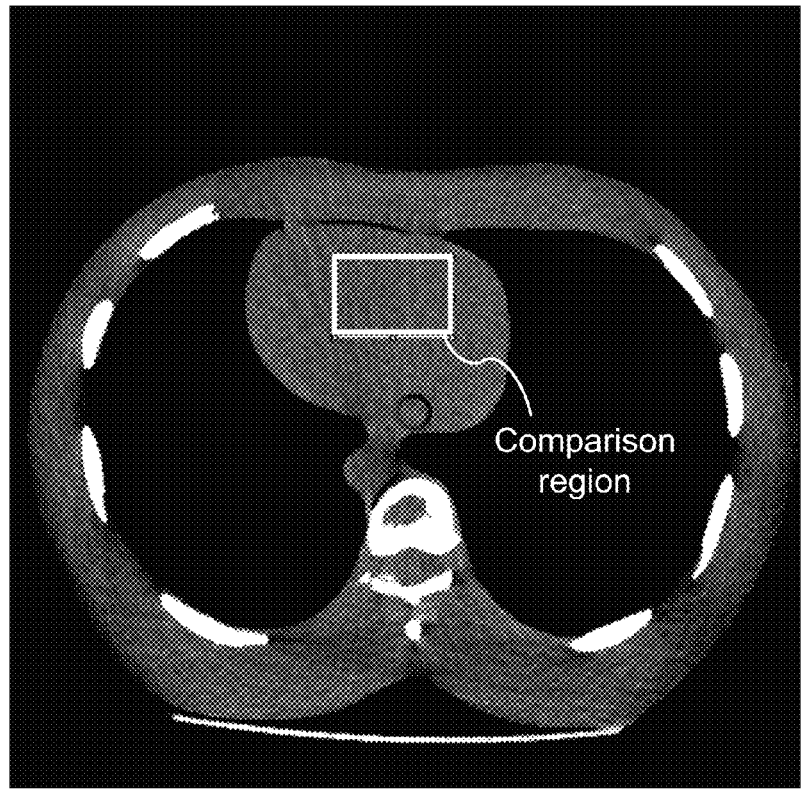
FIG. 8B shows and example of a reconstructed XY-plane image from weighted and gated projection data using an iterative reconstruction (IR) method, wherein the image is slice number 160 of 320 slices.

FIG. 8A shows an example of a reconstructed image created using Taguchi weighting values and FBP. The reconstructed images are plotted on a pixel grid of 512×512. The projection data used to reconstruct the image in FIG. 8A corresponds to cone-beam projections, and FIG. 8A shows a center slice of the cone beam (i.e., slice number 160 out of 320 total slices). For comparison to the FBP image, FIG. 8B shows an IR reconstructed image corresponding to the same center slice of the cone beam. The IR image was reconstructed by minimizing a cost function including a data-fidelity term and a TV-regularization term. Like the FBP image, the Taguchi weighting values were used to reconstruct the IR image. Specifically, the data-fidelity term includes the weighted inner product of the system matrix equation, wherein the diagonal weighting matrix includes the same Taguchi weighting values used in calculating the image shown in FIG. 8A. As can be seen by comparing FIG. 8A and FIG. 8B, the IR method used to obtain FIG. 8B has several advantages over the FBP method used to obtain FIG. 8A. For example, a comparison region having an approximately constant absorption value is selected in both FIGS. 8A and 8B—the white square region. Within this comparison region a standard deviation is calculated for each image resulting in a value of 24.6 HU for FIG. 8A and a value of 8.5 HU for FIG. 8B, revealing approximately a three times reduction in the noise level when the IR method is used.

Figure 9A:
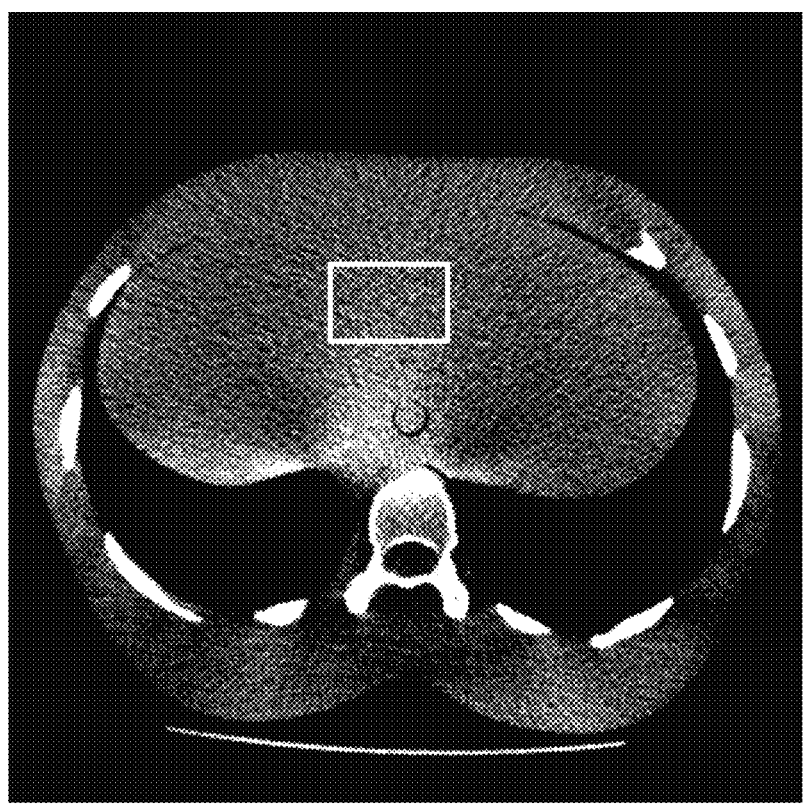
FIG. 9A shows and example of a reconstructed XY-plane image from weighted and gated projection data using a FBP method, wherein the image is slice number 60 of 320 slices.
Figure 9B:
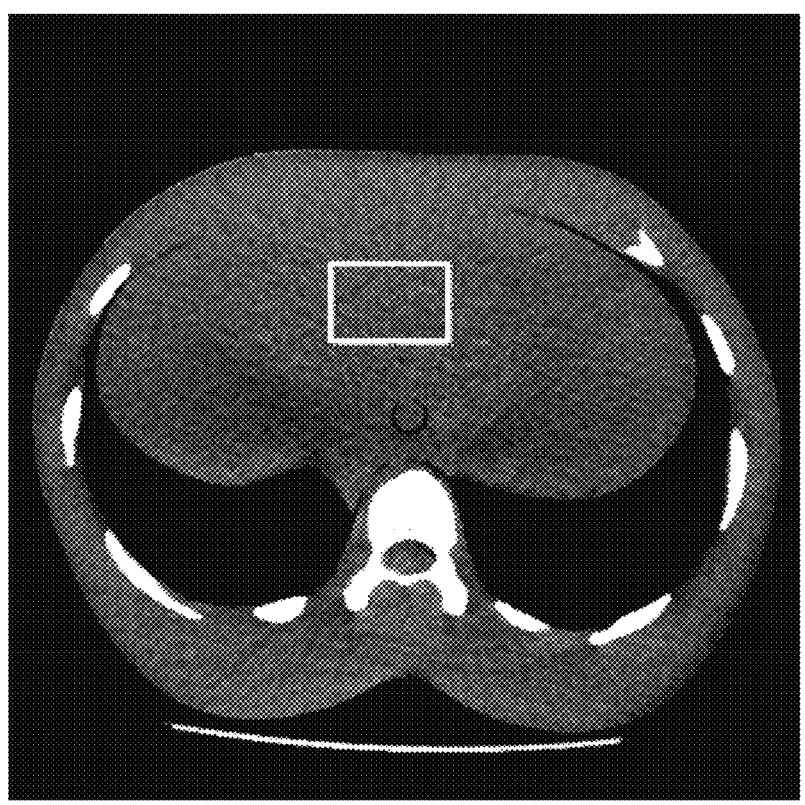
FIG. 9B shows and example of a reconstructed XY-plane from weighted and gated projection data using an IR method, wherein the image is slice number 60 of 320 slices.

FIGS. 9A and 9B show reconstructed images of the $60^{th}$ slice out of 320 slices reconstructed using FBP and IR respectively. The standard deviation within the comparison regions of FIGS. 9A and 9B are respectively 36.9 and 12.9, again revealing a noise improvement of approximately three times for the IR method over the FBP reconstruction method. Further FIG. 9A reveals a low-frequency shading artifact that is commonly observed for away-from-center slices in cone-beam reconstructed images. Using the IR method also mitigates these low-frequency shading artifacts.

Figure 10A:
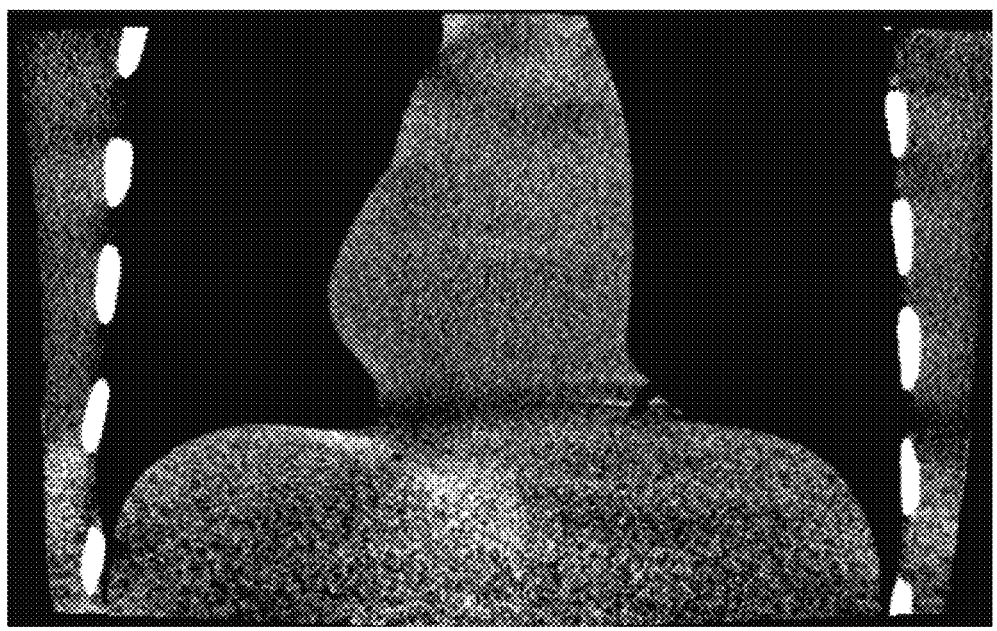
FIG. 10A shows and example of a reconstructed YZ-plane image from weighted and gated projection data using a FBP method, wherein the image is slice number 236 of 512 slices.
Figure 10B:
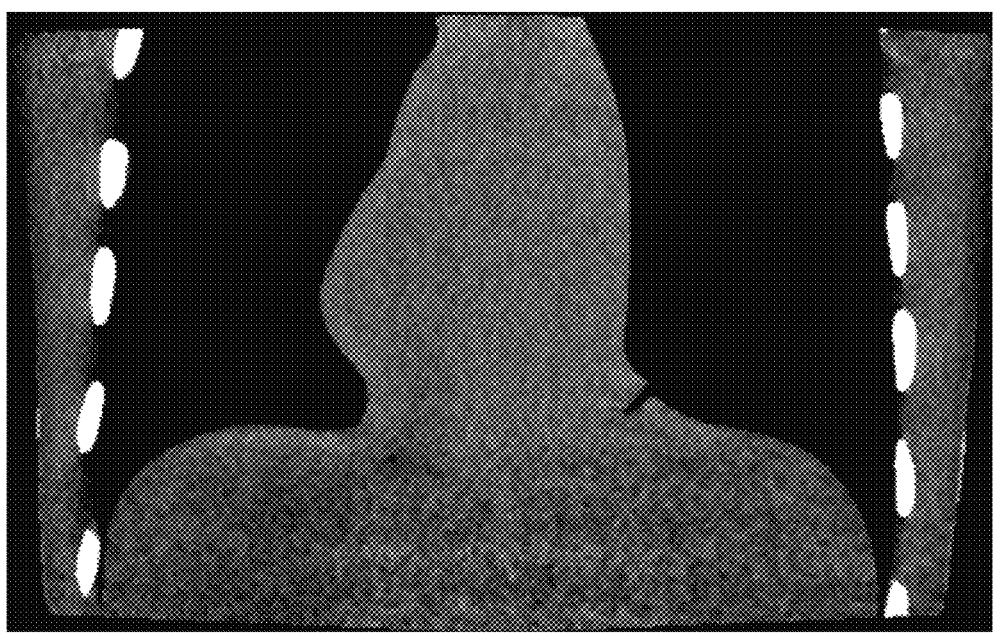
FIG. 10B shows and example of a reconstructed YZ-plane image from weighted and gated projection data using an IR method, wherein the image is slice number 236 of 512 slices.

FIGS. 8A, 8B, 9A, and 9B show XY planes of the reconstructed three-dimensional images. It is also helpful to compare images in the XZ and YZ planes in order to visualize the improvements of the IR method over the FBP method. FIGS. 10A and 10B show YZ plane images obtained using the FBP and IR methods, respectively. These figures are plotted on a pixel grid of 512×320. In the YZ plane, the low-frequency shading artifact is observable in the FBP image (i.e., FIG. 10A), but the low-frequency shading artifacts are significantly reduced in the IR image (shown in FIG. 10B).

Figure 11A:
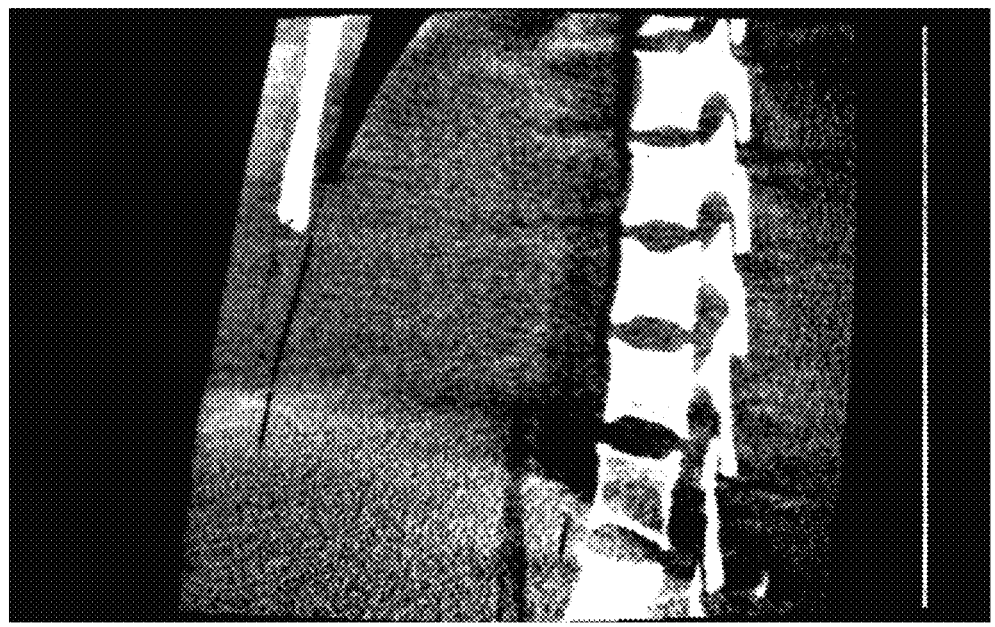
FIG. 11A shows and example of a reconstructed XZ-plane image from weighted and gated projection data using a FBP method, wherein the image is slice number 264 of 512 slices.
Figure 11B:
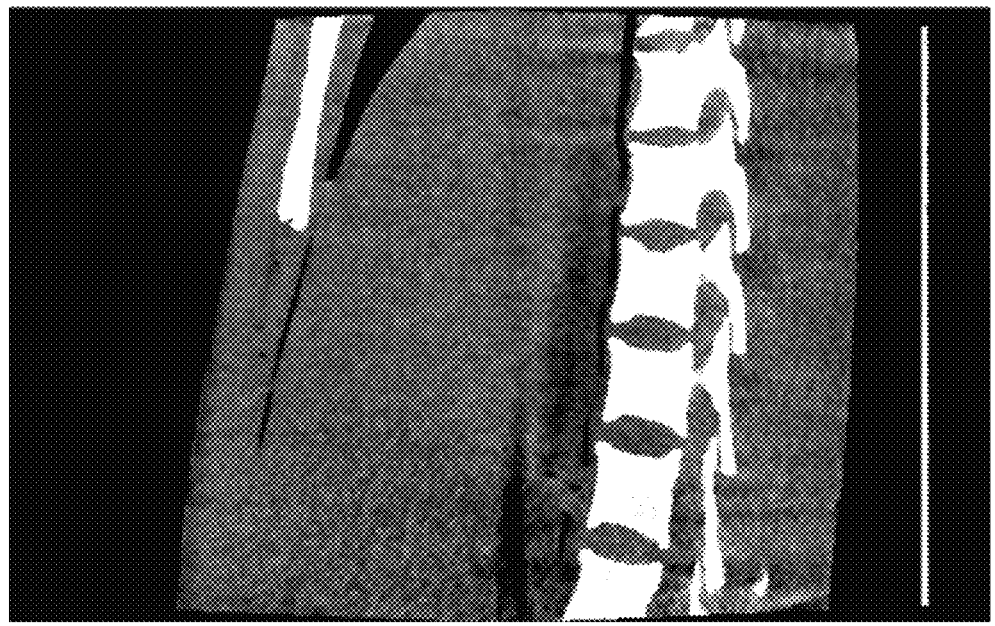
FIG. 11B shows and example of a reconstructed XZ-plane image from weighted and gated projection data using an IR method, wherein the image is slice number 264 of 512 slices.

Similarly, FIGS. 11A and 11B show the XZ plane, and exemplify that the IR method overcomes the low-frequency shading artifact and the noise observed in the FBP image.

The examples herein are primarily directed to cone-beam CT. However, this choice is non-limiting, and method 300 is also applicable for a stacked/parallel fan beam, for example. Further, the gate signal is not limited to an ECG signal and could be any signal, such as, e.g., signals related to cardiac or respiratory motion.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A computed tomography (CT) apparatus, comprising:
processing circuitry configured to
  obtain projection data representing an irradiance of radiation detected at a plurality of detectors and corresponding to a plurality of projection angles of a radiation source;
  obtain agate signal;
  select a subset of the projection data to be gated projection data corresponding to gated projection angles indicated by the gate signal;
  determine weighting-and-feathering coefficients according to the gated projections angles, the weighting-and-feathering coefficients mitigating an inequality of data redundancy of the gated projection data, wherein the inequality of the data redundancy is mitigated by increasing a first coefficient of the weighting-and-feathering coefficients above a threshold in relation to a second coefficient of the weighting-and-feathering coefficients being below the threshold, and a projection angle of the first coefficient being opposite to a projection angle of the second coefficient;
  reconstruct a tomographic image from the gated projection data using an iterative reconstruction method including a regularization term and using the weighting-and-feathering coefficients.

2. The CT apparatus according to claim 1, wherein the processing circuitry is further configured to reconstruct the tomographic image by minimizing a cost function including a first cost-function term that is a weighted inner product of a system matrix equation corresponding to the gated projection data and a second cost-function term that is the regularization term.

3. The CT apparatus according to claim 2, wherein the weighted inner product of the first cost-function term includes a weighting matrix comprising the weighting-and-feathering coefficients along the diagonal of the weighting matrix.

4. The CT apparatus according to claim 2, wherein the weighted inner product of the first cost-function term includes a weighting matrix comprising a product of a diagonal matrix of the weighting-and-feathering coefficients and a statistical weighting matrix representing the uncertainty of the gated projection data.

5. The CT apparatus according to claim 1, wherein the weighting-and-feathering coefficients are determined using a weighting method that is one of a Taguchi weight method, a Parker weight method, a Katsevich weight method, and a Feldkamp weight method.

6. The CT apparatus according to claim 2, wherein the cost function is minimized using an optimization method that is one of a gradient search method, an affine projection method, a primal-dual optimization method, a forward-backward proximal splitting method, a Douglas-Rachford splitting method, an alternating direction method of multipliers, a Korpelevich extragradient method, an Arrow-Hurwicz method, a Nesterov's smoothing method, and a Chambolle-Pock primal-dual.

7. The CT apparatus according to claim 1, wherein the regularization term is one of a projection on convex sets regularization term; a total variation minimization regularization term, a quadratic regularization term, an edge-preserving regularization term, a Gaussian Markov Random Field regularization term.

8. The CT apparatus according to claim 1, wherein the gate signal derives from an electrocardiographic signal.

9. The CT apparatus according to claim 1, wherein the projection data represent the irradiance of one of a cone beam and a parallel fan beam.

10. The CT apparatus according to claim 1, further comprising:
a radiation source radiating the radiation into an object space;
the plurality of detector elements configured to detect the radiation transmitted from the radiation source and through the object space, wherein the plurality of detector elements are configured to generate the projection data; and
a rotation mount configured to rotate the radiation source around the object space, wherein the radiation source is fixedly connected to the rotation mount.

11. A method, comprising:
obtaining projection data representing an irradiance of radiation detected at a plurality of detectors and corresponding to a plurality of projection angles of a radiation source;
obtaining a gate signal;
selecting a subset of the projection data to be gated projection data corresponding to gated projection angles indicated by the gate signal;
determining weighting-and-feathering coefficients according to the gated projections angles, the weighting-and-feathering coefficients mitigating an inequality of data redundancy of the gated projection data, wherein the inequality of the data redundancy is mitigated by increasing a first coefficient of the weighting-and-feathering coefficients above a threshold in relation to a second coefficient of the weighting-and-feathering coefficients being below the threshold, and a projection angle of the first coefficient being opposite to a projection angle of the second coefficient;

reconstructing a tomographic image from the gated projection data using an iterative reconstruction method including a regularization term and using the weighting-and-feathering coefficients.

12. The method according to claim 11, wherein the step of reconstructing the tomographic image further comprises minimizing a cost function including a first cost-function term that is a weighted inner product of a system matrix equation corresponding to the gated projection data and a second cost-function term that is the regularization term.

13. The method according to claim 12, wherein the weighted inner product of the first cost-function term includes a weighting matrix comprising the weighting-and-feathering coefficients along the diagonal of the weighting matrix.

14. The method according to claim 12, wherein the weighted inner product of the first cost-function term includes a weighting matrix comprising a product of a diagonal matrix of the weighting-and-feathering coefficients and a statistical weighting matrix representing the uncertainty of the gated projection data.

15. The method according to claim 11, wherein the step of determining weighting-and-feathering coefficients further comprises determining the weighting-and-feathering coefficients using a weighting method that is one of a Taguchi weight method, a Parker weight method, a Katsevich weight method, and a Feldkamp weight method.

16. The method according to claim 12, wherein cost function is minimized using an optimization method that is one of a gradient search method, an affine projection method, a primal-dual optimization method, a forward-backward proximal splitting method, a Douglas-Rachford splitting method, an alternating direction method of multipliers, a Korpelevich extragradient method, an Arrow-Hurwicz method, a Nesterov's smoothing method, and a Chambolle-Pock primal-dual.

17. The method according to claim 11, wherein the regularization term is one of a projection on convex sets regularization term, a total variation minimization regularization term, a quadratic regularization term, an edge-preserving regularization term, a Gaussian Markov Random Field regularization term.

18. The method according to claim 11, wherein
the step of obtaining the gate signal further comprises deriving the gate signal from an electrocardiographic signal; and
the step of obtaining the projection data further comprises that the projection data represent the irradiance of one of a cone beam and a parallel fan beam.

19. An image-processing apparatus, comprising:
processing circuitry configured to
obtain projection data representing an irradiance of radiation detected at a plurality of detectors and corresponding to a plurality of projection angles of a radiation source;
obtain a gate signal;
select a subset of the projection data to be gated projection data corresponding to gated projection angles indicated by the gate signal;
determine, weighting-and-feathering coefficients according to the gated projections angles, the weighting-and-feathering coefficients mitigating an inequality of data redundancy of the gated projection data, wherein the inequality of the data redundancy is mitigated by increasing a first coefficient of the weighting-and-feathering coefficients above a threshold in relation to a second coefficient of the weighting-and-feathering coefficients being below the threshold, and a projection angle of the first coefficient being opposite to a projection angle of the second coefficient;
reconstruct a tomographic image from the gated projection data using an iterative reconstruction method including a regularization term and using the weighting-and-feathering coefficients.

20. A non-transitory computer-readable medium storing executable instructions, wherein the instructions, when executed by processing circuitry, cause the processing circuitry to perform the method according to claim 11.

* * * * *